United States Patent [19]

Kokesh

[11] 4,357,836
[45] Nov. 9, 1982

[54] SAMPLE INJECTION SYSTEM FOR CHEMICAL ANALYZER AND METHOD OF SAMPLE ANALYSIS

[75] Inventor: Fritz C. Kokesh, Bartlesville, Okla.

[73] Assignee: Phillips Petroleum Company, Bartlesville, Okla.

[21] Appl. No.: 218,231

[22] Filed: Dec. 19, 1980

[51] Int. Cl.³ .......................................... G01N 35/00
[52] U.S. Cl. .................................................. 73/863.11
[58] Field of Search .......... 73/863.11, 863.12, 864.81, 73/864.82, 864.83; 422/78, 79, 80

[56] References Cited

U.S. PATENT DOCUMENTS

| | | | |
|---|---|---|---|
| 3,053,077 | 9/1962 | Tracht | 73/23 |
| 3,118,300 | 1/1964 | Jenkins | 73/23 |
| 3,205,701 | 9/1965 | Szonntagh | 73/23.1 |
| 3,304,159 | 2/1967 | Hinsvark . | |
| 3,327,520 | 6/1967 | Stapp | 73/23.1 |
| 3,366,149 | 1/1968 | Taft | 141/82 |
| 3,463,012 | 10/1969 | McKinney | 73/422 |
| 3,482,450 | 12/1969 | Harris | 73/422 |
| 3,498,107 | 3/1970 | Kim | 73/23.1 |
| 3,518,059 | 6/1970 | Levy | 23/232 |
| 3,592,046 | 7/1971 | Cramers | 73/23.1 |
| 3,592,064 | 7/1971 | Gether | 73/422 |
| 3,904,366 | 9/1975 | Grasenick | 422/78 |
| 4,035,168 | 7/1977 | Jennings | 55/67 |
| 4,084,440 | 4/1978 | Carpenter | 73/422 |
| 4,153,415 | 5/1979 | Espitalie | 23/230 |
| 4,159,894 | 7/1979 | Hu | 23/230 |
| 4,229,181 | 10/1980 | Espitalie et al. | 422/80 |
| 4,244,917 | 1/1981 | Woods | 422/78 |
| 4,262,533 | 4/1981 | Jeager | 73/863.11 |

OTHER PUBLICATIONS

*Barker,* Pyrolysis Techniques For Source Rock Evaluation, Amer. Assoc. Pet. Geol. Bull., pp. 2349–2361 (1974).
*Espitalie,* Source Rock Characterization Method For Petroleum Exploration, Paper Presented 5-2-77 In Houston, Texas.
*Barker,* Pyrolysis Techniques For Source Rock Evaluation, Unpublished Report.
*Clements,* Wellsite Geochemistry By Programmed Pyrolysis (1979).
*Welte,* Hydrocarbon Source Rocks In Deep Sea Sediments (1979).
*Giraud,* Application Of Pyrolysis And Gas Chromatography To Geochemical Characterization, Amer. Assoc. Petr. Geol. Bull., vol. 54, pp. 439–455 (1970).

*Primary Examiner*—S. Clement Swisher

[57] ABSTRACT

A sample injection system for a gas chromatograph or other analysis instrument and a method of sample analysis are described. The injection system comprises a sample chamber, a sample inlet at one end of the sample chamber, a sample outlet at the opposite end of the sample chamber, means for cooling the sample chamber and means for introduction of a carrier gas into the sample chamber. In one embodiment, the injection system further includes a second sample chamber openly connected with the first sample chamber so as to allow the transfer of a solid or liquid sample from the first chamber wherein the sample can be contacted at ambient temperature with a flowing carrier gas, to a preheated second chamber, wherein hydrocarbons are thermally extracted from the sample. The injection system and method are particularly suited for thermal analysis of geological samples to obtain information useful in petroleum exploration.

42 Claims, 6 Drawing Figures

SAMPLE INJECTION SYSTEM FOR CHEMICAL ANALYZER AND METHOD OF SAMPLE ANALYSIS

BACKGROUND OF THE INVENTION

This invention relates to a method and apparatus for the chemical analysis of matter. In one aspect, it relates to the determination of the quantity of volatile hydrocarbons and the hydrocarbon generating potential of the insoluble organic material or kerogen present in a geological sample. The invention relates in another aspect to an injection system for a gas chromatograph or other analytical instrument.

In the field of geochemical research and petroleum exploration, an area of growing interest is the analysis of geological samples to determine the remaining petroleum-generating potential of these samples. Work in this field has been directed to methods for removing hydrocarbons from geological samples and analyzing the hydrocarbons, to apparatus for laboratory and field analysis of geological samples, and to the development of theoretical and practical models that allow the raw data obtained to be used for purposes of petroleum exploration. A method known in the art for such analyses involves the thermal extraction of volatile hydrocarbons from a kerogen (insoluble organic portion of a sedimentary rock) or rock sample followed by pyrolysis of the remaining organic material. Conventional methods such as flame ionization detection can be used to determine the quantity of hydrocarbons generated in each operation, and the information thus obtained can be used to determine certain petroleum exploration-related characteristics of the sample.

A pyrolysis unit, or modified gas chromatograph, is used for such thermal analytical methods. A rock sample is placed in a sample inlet which has been heated to the temperature of hydrocarbon volatilization. The sample is subsequently heated to a higher temperature, generally by means of a radiant heater, to pyrolyze the remaining organic matter. A gas detection device such as a flame ionization detector responds to the quantity of hydrocarbons generated and a recorder instrument records graphically the detector response versus time. The detector responses obtained are compared with standards developed to determine the actual quantities of hydrocarbons generated, and to thus assess the petroleum potential of the sample.

In performing analyses of the type described above, it is desirable to be able to make accurate, reproducible determinations of the quantity of volatile hydrocarbons present in the geological sample. It is also desirable, both for economic reasons and for performing rock sample analyses in the field, to have analytical equipment which is simple and compact.

It is therefore an object of the invention to provide an improved apparatus for thermal analysis of solids and liquids.

It is a further object of the invention to enable more accurate determination of the remaining hydrocarbon generating potential of the insoluble organic matter.

SUMMARY OF THE INVENTION

According to the invention, a sample receptacle for an analytical instrument such as a gas chromatograph is provided, the sample receptacle comprising a sample chamber, a sample inlet at one end of the sample chamber, a sample outlet at the opposite end of the sample chamber, means for cooling the sample chamber, and means for introducing a carrier gas into the sample chamber. According to one embodiment of the invention, the sample receptacle comprises a longitudinally-extended tubular inner chamber having a sample inlet at one end of the chamber and a sample outlet at the opposite end of the chamber, means for introducing a carrier gas into the chamber, a jacket surrounding and spaced apart from the tube defining the inner chamber, the jacket and tube defining an annular space, means for introducing a cooling fluid into one end of the annular space, and means for removing the cooling fluid at the opposite end of the annular space. The annular space may include means such as a spiraling baffle to ensure the smooth flow of cooling fluid therein and to increase cooling efficiency.

Also according to the invention, an injection system for an analytical instrument such as a gas chromatograph is provided, the injection system comprising a first chamber and a second chamber, a sample inlet to the first chamber, a sample outlet extending openly into the second chamber, means for cooling the first chamber, means for introducing a carrier gas into the first chamber, and a second chamber gas outlet. According to one embodiment of the invention, the injection system comprises first and second zones, the first zone being a sample receptacle as described above and the second zone being openly connected to the first zone so as to permit the uninterrupted flow of a carrier gas through both zones and the physical transfer of a solid or liquid sample from the first zone to the second zone. The injection system is preferably a single, continuous horizontally-extended tube having a sample inlet at one end and a gas outlet at the opposite end, the first chamber being defined by the portion of the horizontally-extended tube which includes means for cooling the interior space of the tube and the second chamber being defined by the remainder of the tube.

In a further embodiment of the invention, an analytical instrument is provided which comprises a sample injection system having separate cooled and heated zones, a detector device, and conduit means for gas flow between the heated zone of the injection system of the detector device. According to one embodiment of the invention, the analytical instrument is a pyrolysis unit comprising a sample injection system having an outer cooled chamber and an inner heated chamber, means for heating the inner heated chamber, at least one gas detection device, and means for gas flow from the cooled chamber through the heated chamber to the detection device.

In a thermal analysis method in which a solid or liquid sample is heated to thermally extract volatile hydrocarbons therefrom, the volatilized hydrocarbons being passed in a carrier gas to a detector capable of sending a response signal indicative of a qualitative or quantitative characteristic of the volatilized hydrocarbons, the invention method comprises placing the sample in the flow path of the carrier gas while maintaining the sample at a temperature lower than the volatilization temperature of the volatile hydrocarbons therein and allowing the carrier gas to flow in contact with the sample for a sufficient time to permit stabilization of the detector response prior to heating the sample to the hydrocarbon volatilization temperature.

In the invention analysis method practiced with the invention apparatus, a sample in a suitable holder is positioned in the cooled anterior zone of the sample injection system and a carrier gas is allowed to flow across the sample and through the heated interior zone of the injector to a detector which responds to a change in the quality or quantity of the gases in the carrier gas and activates a signal generating and recording device. After a sufficient time to establish a stabilized output signal from the detector following insertion of the sample, the sample is transferred to the heated interior zone of the injector while maintaining the flow of the carrier gas across the sample and to the detector. If the sample is a geological sample being analyzed to determine its petroleum-generating potential, the interior zone will be preheated to a temperature effective in volatilizing volatile hydrocarbons in the sample. Following a sufficient amount of time for a signal representative of the quantity of volatile hydrocarbons thermally extracted from the sample to be recorded, the sample is heated, preferably under controlled conditions to provide a constant rate of temperature increase, to a temperature effective for pyrolyzing the sample. The products generated by pyrolysis are passed to the detector by means of the carrier gas, and a signal representative of the quantity of product is recorded. Computational manipulation of the thus-obtained quantities of volatile and pyrolysis products can provide a guide for determining the petroleum-generating capability of the sample.

The invention injection system replaces conventional gas chromatograph injectors and provides an improvement in the reproducibility and accuracy of the results obtained when geological samples are analyzed by thermal extraction and pyrolysis. The sample is purged of air and other contaminants and is not re-exposed to air prior to being inserted into the heating chamber for thermal extraction. The unitary construction of the cooled chamber and the heated chamber of the injector also offers advantages in accuracy of results and convenience over conventional "interface" devices which do not allow transfer of the sample itself into the preheated zone of the gas chromatograph and which have exposed conduits extending from the interface device to the temperature-controlled chamber of the gas chromatograph which are subject to the problem of vapor condensation therein. The invention injector provides a reasonably simple device which can be used in present conventional gas chromatographs or pyrolysis units in the laboratory or in the field.

DETAILED DESCRIPTION OF THE INVENTION

The sample injection system of the invention comprises at least two zones or chambers in series, into which a solid or liquid sample can be inserted for analyses involving sequential operations requiring different temperatures. The first chamber into which a sample is inserted will be referred to herein as the "anterior chamber" or "cooled chamber," the latter referring to the fact that in normal operation this area of the device will be maintained at a desired temperature by cooling means which constitute a part of the sample injection system. When described as a unit apart from the remainder of the sample injection system, the cooled chamber will be referred to as a "sample receptacle" for an analytical instrument. The second chamber or zone in the sample injection system is referred to herein as the "interior chamber" or "heated chamber," the latter referring to the fact that in use in thermal analyses this area of the sample injection system will be maintained at an elevated temperature.

A preferred embodiment of the sample injection system for a gas chromatograph or or other analytical instrument is shown in FIGS. 1–4. The anterior sample receptacle 1 provides a chamber 2 into which a solid or liquid sample can be inserted and held at a temperature which is lower than that at which volatile hydrocarbons in the sample are released. The sample is introduced via sample inlet 3 which is shown with a gas-proof fitting to which can be attached means to close the chamber to the outside.

Figure 4:
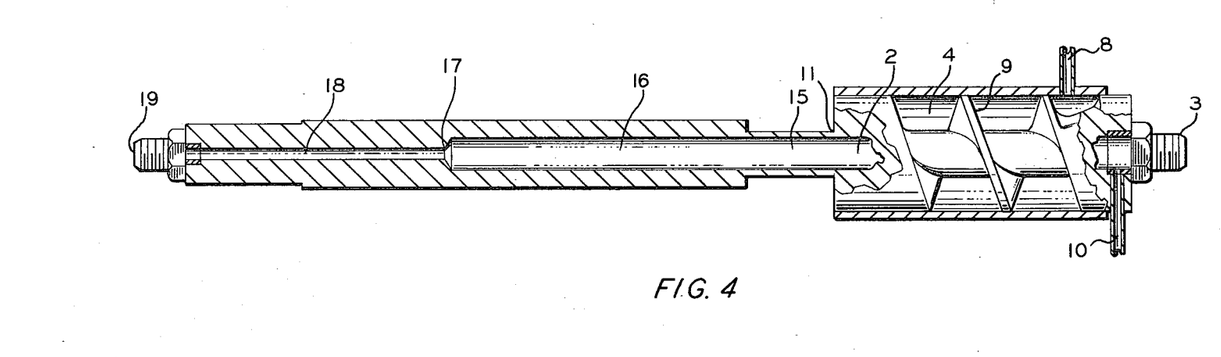
FIG. 4 is a cross-sectional view taken along lines 4—4 of FIG. 1.

Cooling is provided by indirect heat exchange with a fluid flowing in annular space 4 between tubular member 5 defining the exterior chamber 2 and an outer cylindrical jacket 6 which is provided with a cooling fluid inlet 7, preferably located near the outlet end of chamber 2, and cooling fluid outlet 8, shown in FIG. 4, preferably located near the inlet end of chamber 2. The cooling fluid is preferably a gas at room temperature such as air. In the embodiment shown, the cooling effect of the fluid is enhanced by the presence of means to direct the flow of the fluid through the annular space such as the spiral baffles represented by reference numeral 9.

A carrier gas inlet 10 admits a carrier gas such as helium into the inlet end of sample chamber 2. The carrier gas inlet is connected to a source of carrier gas (not shown) and pressure regulation device to maintain a constant flow rate of the carrier gas through sample chamber 2.

Sample outlet 11 of chamber 2 is of sufficient size for removal of a solid sample from the cooled area or for convenient transfer of a solid sample from the cooled chamber to an adjacent chamber of the sample injection system shown. The sample outlet is preferably a circular orifice having a diameter substantially equal to the diameter of the tubular sample chamber. The sample outlet 11 can be modified with connecting means for attachment of such an anterior sample receptacle to a sample inlet port of a gas chromatograph or other instrument.

Figure 3:
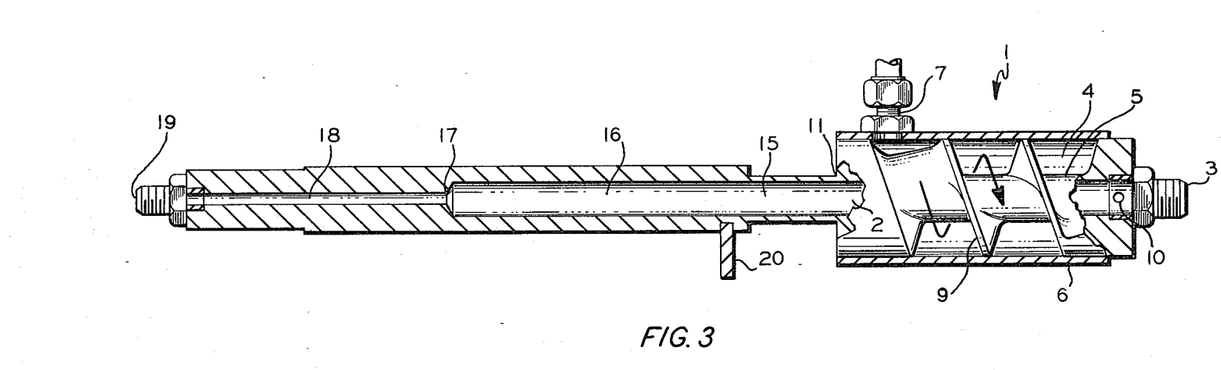
FIG. 3 is a cross-sectional view taken along lines 3—3 of FIG. 2.

Sample outlet 11 of first chamber 2 opens into the optional intermediate chamber 15 and therethrough into second chamber 16. As shown in FIGS. 3 and 4, the first and second chambers are defined by tubes having an interior diameter and an external radius. The interior tubular diameters of chambers 15 and 16 are large enough to permit insertion of a solid sample of suitable size for analysis by the instrument being used. Preferably, for ease of sample insertion and transfer within the injector and for smooth flow of the carrier fluid, the diameters of chambers 2, 15 and 16 are substantially equal. The illustrated sample injection system thus includes three chambers within a single, continuous bore or tube, the first chamber being defined by the area cooled by indirect heat exchange with the cooling fluid flowing in annular space 4, the second chamber being directly adjacent to the first chamber or openly connected to its outlet end via an optional intermediate chamber which can have a reduced outer tubular radius, this intermediate chamber providing insulation between the second chamber, which is at a substantially elevated temperature in normal use of the injector, and the first chamber, which is maintained at about room temperature during the sample purging process, described below.

Second sample chamber 16 extends to an outlet 17, through which the carrier gas and released gases to be analyzed flow to a detector (not shown), optionally via a conduit 18 and a gas outlet 19 in the sample injection device. Conduit 18 preferably has a reduced diameter for gas flow from the sample chambers to the detector and gas outlet 19 may be connected to one or more detectors via other conduits, not shown. If desired for the particular analysis being performed, gases exiting second sample chamber 16 can be passed to a detector through a gas chromatograph column.

The injection system having separate cooled and heated zones can replace the standard injector of a conventional gas chromatograph or pyrolysis unit. The invention injector can be equipped with thermocouples whereby the temperature within the cooled zone can be monitored. When installed in a gas chromatograph, guide pin 20 serves as means for positioning and stabilizing the injector within the instrument. When the injector is properly positioned in the gas chromatograph or pyrolysis unit, the exterior wall of second chamber 16 is generally adjacent to a heating block or other heating means in the instrument. The sample injection device will generally be installed so that the anterior chamber extends outwardly from the instrument and is not enclosed within the walls of the instrument. The design of the injector allows a substantial temperature differential to be maintained between the anterior chamber, wherein the sample can be purged with carrier gas at about room temperature, and the interior chamber, which is often maintained at a substantially elevated temperature such as 300° C. The purged sample can be inserted directly into the preheated chamber without contact with air or other sources of contamination.

Figure 1:
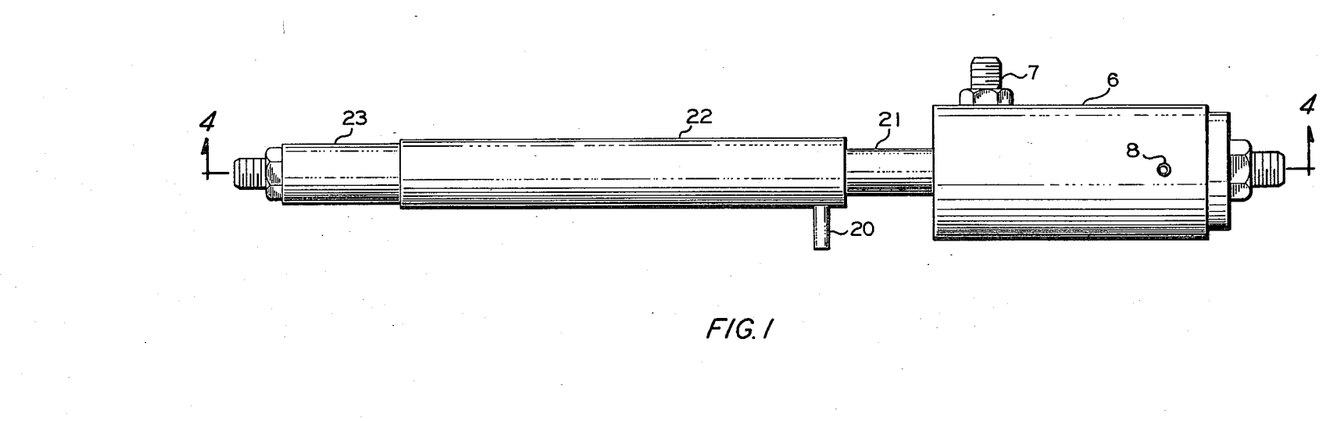
FIG. 1 is an elevation of one embodiment of the sample injector.
Figure 2:
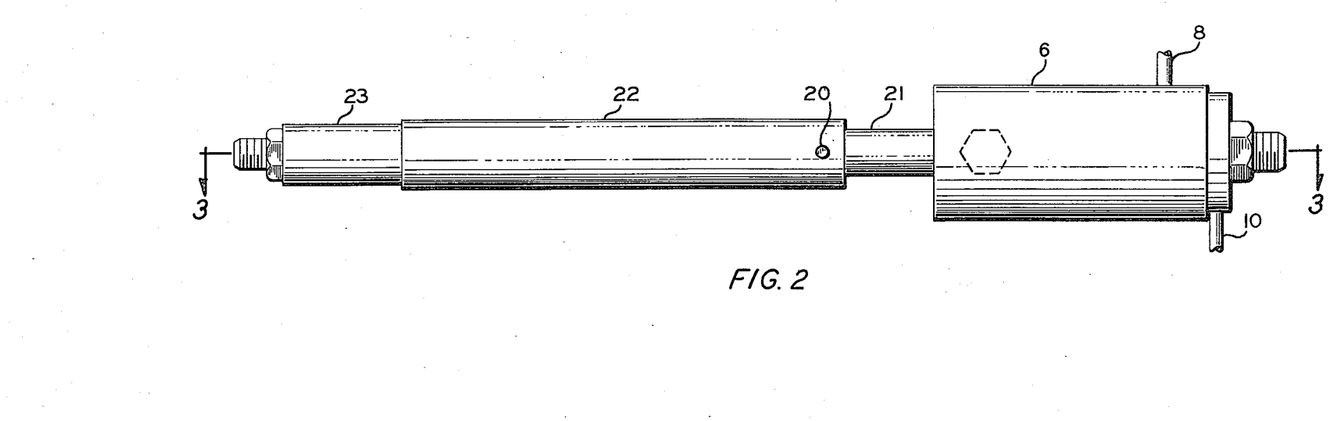
FIG. 2 is an elevation of the sample injector of FIG. 1 rotated 90° along its longitudinal axis.

FIGS. 1 and 2 show the exterior of a sample injection device for a gas chromatograph or other analytical instrument. Cylindrical jacket 6 provides an exterior wall for the annular space surrounding the first sample chamber. The tubular length of reduced exterior radius 21 extends between the first chamber and the second sample chamber, which is within cylindrical enclosure 22. Guide pin 20, which provides means for positioning the sample injection device within an analytical instrument, is located on the cylindrical enclosure so as to position the cooled zone within jacket 6 outside the heating block or other heating means of the instrument. Gas-tight fitting means 7 provides a cooling fluid inlet to the annular space within jacket 6. Conduit 8 (FIG. 2) provides a cooling fluid outlet. Conduit 10 connects a source of carrier gas (not shown) with the first sample chamber, located in a separate enclosure within jacket 6.

Tubular length 23, which is shown as a tubular length of reduced exterior diameter, will generally enclose at least a portion of the conduit means for carrier gas flow between the heated chamber and the detector of the analytical instrument.

The dimensions of the sample injection device can vary widely depending upon the the instrument to which it is attached, the type of analysis being performed and the sample size. When designed for a conventional pyrolysis unit for the analysis of small rock samples which are positioned in the injector by means of an inserted device having a radiant heater, for example, the inner diameter of the anterior or cooled chamber will generally range from about $\frac{1}{8}$-inch to about $\frac{1}{2}$-inch; the length of the anterior chamber will generally be in the range of about 2 to about 3 inches; the length of the interior or heated chamber will generally be about 2 to about 3 inches; and the intermediate insulating chamber, if present, will range from about $\frac{1}{2}$-inch to about $1\frac{1}{2}$ inches in length. The inner diameter of the conduit from the heating chamber outlet of the detector, represented by reference numeral 18 in FIG. 4, will generally range from about 1/16-inch to about $\frac{1}{4}$-inch in diameter and will be about $1\frac{3}{4}$ inch to about $2\frac{3}{4}$ inch in length. These dimensions are intended only to provide guidance in designing and using the injector but are not intended to be limiting, as the size of the injector and the dimensions of its constituent parts can vary depending upon the use to which it is applied.

ANALYSIS METHOD

The sample analysis method of the invention can be applied to thermal analyses of solid or liquid samples wherein a sample is inserted into an oven or other heated zone of a gas chromatograph and the resulting thermally-extracted material is transported by a carrier gas to a detector for quantitative or qualitative analysis. The invention method permits more accurate and reproducible sample analyses by providing a preliminary operation in which the sample is inserted into the carrier gas flow stream in a section of the gas chromatograph or other analysis instrument maintained at a temperature lower than the temperature at which the volatile components of the sample are driven off. The sample is left in this cool zone for a time effective in removing contaminants from the sample insertion/holding means, as indicated by the stabilization of the detector response following insertion of the sample into the carrier gas stream, which results in a temporary change in the carrier gas flow rate and thus an extraneous detector response which it is desirable to eliminate or minimize from the thermal extraction response data.

The practice of the invention method can best be described by reference to FIG. 5. The description will focus on the use of a pyrolysis unit or a gas chromatograph to analyze a geological sample such as rock or kerogen to determine the petroleum-generating potential of the sample, but the invention method applies to the quantitative or qualitative analysis of any analyzable material for any purpose. The method is particularly appropriate for the thermal extraction of volatile materials from a solid or liquid sample including but not limited to rock, kerogen, polymer, coal, asphaltene, or freeze-dried bacteria.

Figure 5:
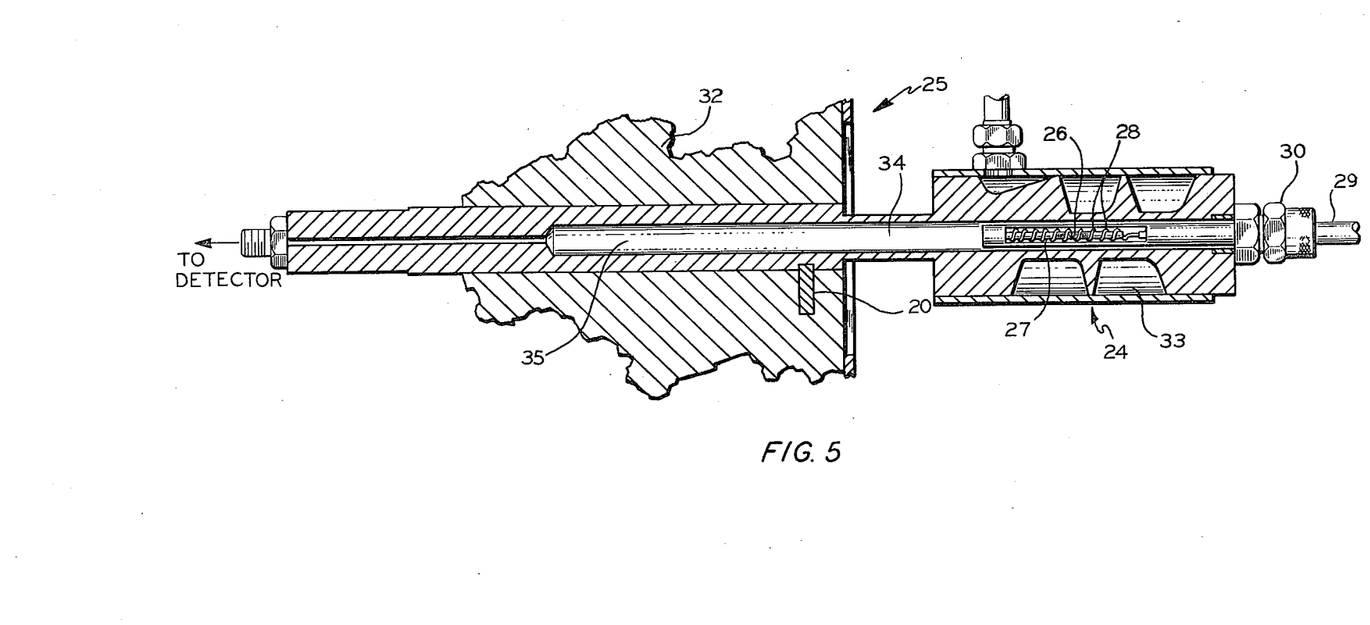
FIG. 5 is a cross-sectional view showing the sample injector installed in an analysis instrument, with a sample insertion means positioned within the injector so that the sample is within the cooled anterior zone.

An accurately weighed sample to be analyzed is placed in a suitable insertion means for placement within the cooled zone of injector apparatus 24 of gas chromatograph 25 shown in FIG. 5. The sample can vary widely in size depending upon the instrument and the analysis to be performed, but a solid sample will generally range in weight from about 0.1 mg to about 20 mg, with the weight of a kerogen sample generally being in the lower end of the range and a rock sample in the upper end. In FIG. 5, rock sample 26 is shown within a sample tube 27 positioned within heating coil 28 of sample insertion means 29. The sample, in small granules or powder form, is conventionally placed in a quartz tube the ends of which are enclosed by gas-permeable quartz felt. The sample insertion means shown is one having a self-contained radiant heater the coil of which also serves to hold the sample tube. Such a sample insertion means is, for example, a Pyroprobe ® heating unit sold by Chemical Data System. The pyrolysis unit can be a Perkin Elmer Model 900B gas chromatograph modified with the invention injection system in place of the standard injection port. The injector is sealed by suitable means such as a Swagelok ® fitting 30 attached to the sample insertion means. In FIG. 5, the sample insertion means is shown locked in place with the sample-containing end positioned in the cooled zone of the sample injection system.

The proximity of heating block 32 of the gas chromatograph to the anterior chamber necessitates the cooling of the anterior chamber during the sample purging step to prevent the volatilizing of hydrocarbons from the sample during this operation. A cooling fluid such as compressed air is forced through annular space 33 to maintain the temperature of the cooled chamber at a temperature lower than the temperature of the heating block, preferably at a temperature of from about 30° C. to about 40° C. Using the arrangement shown in FIG. 5, in which the anterior chamber protrudes from the gas chromatograph and is cooled by compressed air flowing through baffles in the annular space surrounding the anterior chamber, it is possible to maintain a temperature of about 35° C. in the anterior chamber while the heating block, adjacent to the interior chamber, is at its normal operating temperature of about 300° C.

A suitable carrier gas such as helium is introduced into the cooled zone via a conduit (not shown) connected to a carrier gas source and a flow regulator. The carrier gas inlet is preferably located near the sample inlet so that a sample positioned in the cooled zone is downstream of the carrier gas inlet. The flow rate adjustment will vary according to conventional gas chromatography practice, but will generally range from about 20 cc/minute to about 60 cc/minute. The sample is contacted with the flowing carrier gas to purge the sample, as well as the insertion device, of contaminants such as air and water vapor which would otherwise react with the volatile compounds in the heating zone and would therefore destroy or modify the hydrocarbons monitored by the detector thus undermining the accuracy and reproducibility of the analysis. The sample is held in the inlet chamber for at least a time sufficient to allow the detector response to stabilize following the injection of the sample into the purge zone. That is, the sample is retained in the purge zone for a time sufficient for the establishment of a substantially stable response signal from the detector, as conveniently reflected in the form of a substantially level baseline trace from the peak recorder. In using the type of instrument shown in FIG. 5 for thermal extraction of hydrocarbons from a rock sample, a holding time of about 1 to 2 minutes has been found to represent a satisfactory balance of convenience and accuracy.

Following the completion of the purge operation on the sample, the sample is transferred from the cooled anterior chamber to the heated interior chamber 35, via the intermediate insulating zone 34. Interior chamber 35 is preheated so as to be at the desired elevated temperature when the sample is placed into it.

The heated chamber is maintained at a temperature effective for thermal extraction of the volatile hydrocarbons from the sample. Assuming again that a rock sample is being analyzed for thermally extractable hydrocarbons, the sample will be heated to a temperature of about 100° C. to about 400° C., preferably about 250° C. to about 310° C., generally about 300° C. The effluent from the thermal extraction of the sample is carried by the carrier gas to at least one detector such as a flame ionization detector and/or thermal conductivity detector. The hydrocarbons may be passed through a chromatography column if desired for the particular analysis being performed.

The thermal extraction process is usually complete after about 2 to 3 minutes following injection of the sample into the heating chamber. After thermal extraction of the volatile hydrocarbons from the sample, a further heating of the remaining portion of the sample to pyrolyze the remaining organic material is effected. Pyrolysis of the sample is effected by heating it to a temperature effective in destroying the organic material or about 350° to about 1000° C., preferably about 400° to about 900° C. The pyrolysis is conveniently and effectively carried out by activating the heating coil of the insertion device while the sample is within the heated chamber. The temperature of the heating coil is generally raised at a constant rate within the range of about 30° C./minute to about 300° C./minute.

EXAMPLE

A thermal analysis of a Michigan oil shale sample was performed using a conventional Perkin-Elmer Model 900B gas chromatograph that was equipped with a calibrated flame ionization detector (FID), the sample injection system of the invention, a Chemical Data Systems Pyroprobe ® and Series 120/382 Controller, a Perkin-Elmer Sigma-10 Data Station and Interface, and a Leeds and Northrup Speedomax ® Model XL strip chart recorder.

A crushed and dried sample of a Michigan oil shale weighing 4.6 mg was placed into a 0.2×2 cm quartz tube plugged at each end with quartz felt. Both the tube and the quartz felt had been cleaned with distilled-in-glass, reagent-grade pure methylene chloride. The sample tube was then placed within the Pyroprobe heating coil, the sample end of the Pyroprobe was positioned within the exterior chamber of the invention sample injector, and the sample inlet was sealed. The exterior chamber was maintained at about 35° C. by indirect heat exchange with compressed air flowing in the baffled annular space surrounding the exterior chamber. The carrier gas was introduced upstream of the sample and was allowed to flow across the sample for a period of about 1.5 minutes. During this period the FID response was monitored by the strip chart recorder and the Sigma-10 Data Station in order to establish a detector baseline response. After this initial period, the sample was transferred by means of the Pyroprobe from the cooled exterior chamber to the heated interior chamber via the intermediate insulating chamber.

Figure 6:
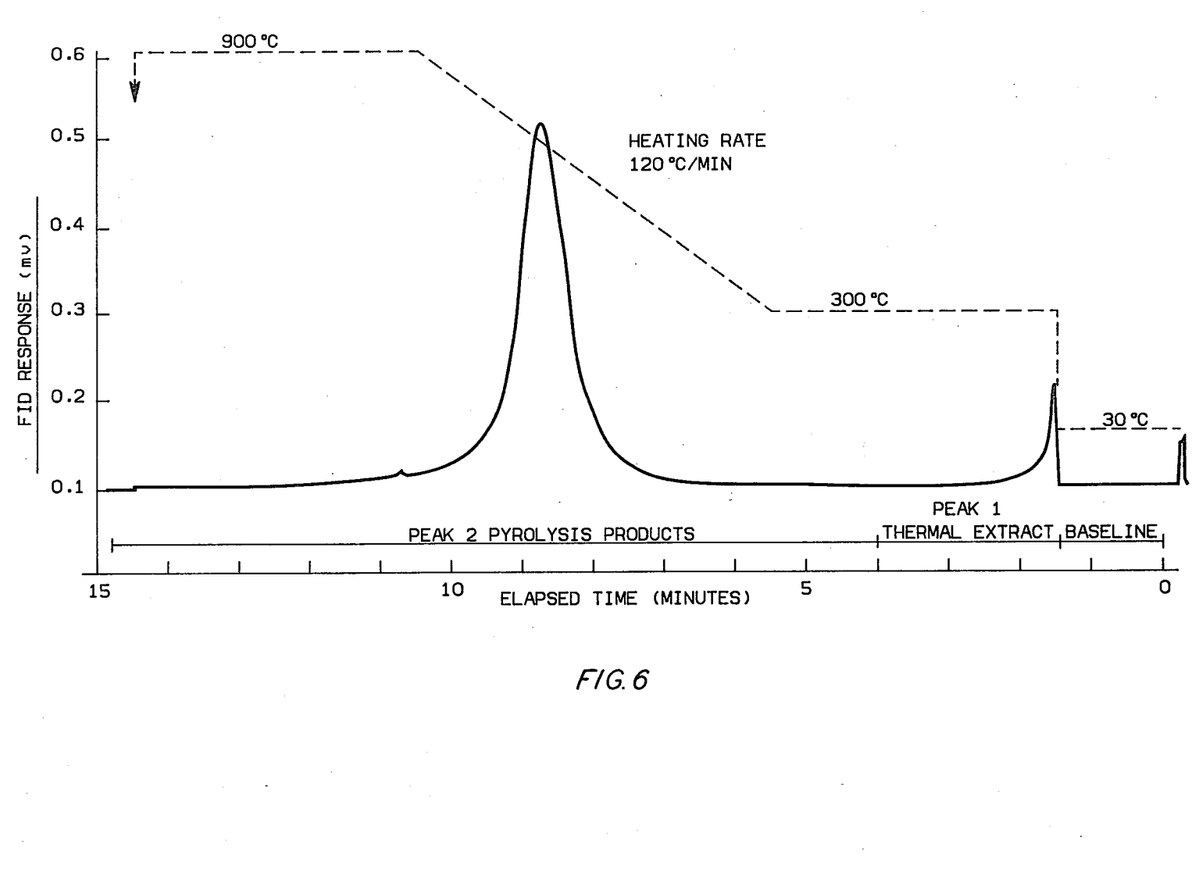
FIG. 6 is a pyrogram showing the charted results (flame ionization response vs. time) of a pyrolysis analysis according to the invention method.

The products released from the sample as a result of thermal extraction in the heated interior chamber caused the FID to produce a signal indicative of released hydrocarbons. The detector signal was amplified and then recorded on the strip chart recorder and by the Sigma-10 Data Station. Referring to FIG. 6 (time scale from right to left), Peak 1, which extends from 1.5 to 4.0 minutes, is due to the detector response during the first heating step in which volatile hydrocarbons were thermally extracted from the rock sample. The Sigma-10 was programmed to calculate the area of Peak 1 (in units of millivoltseconds), and based on the calibration of the FID to convert this area to a hydrocarbon yield (in units of milligrams of hydrocarbon per gram of rock).

After a total elapsed time of 4 minutes, the seond heating stage, or pyrolysis, of the sample was initiated by activating the radiant heater of the Pyroprobe, which was programmed to heat at a rate of 120° C./minute to a final coil temperature of 900° C. Referring to FIG. 6, Peak 2 extends from 4.0 to 15.0 minutes and is due to products formed in the second heating operation in which the sample was pyrolyzed. The Sigma-10 was programmed to determine the area of Peak 2 and to convert this area to a hydrocarbon yield (in units of milligrams of hydrocarbon per gram of rock).

I claim:

1. A sample receptacle for an analytical instrument comprising:
   a sample chamber having a sample inlet for receiving a solid sample and an opposing sample outlet for removal of a solid sample;
   means for cooling the sample chamber; and
   means for introducing a carrier gas into the sample chamber.

2. The sample receptacle of claim 1 wherein the means for cooling the sample chamber comprises means for fluid flow in indirect heat exchange relationship with the sample chamber.

3. The sample receptacle of claim 1 wherein the sample chamber is an elongated cylindrical bore within a tubular member having an inlet end and an outlet end.

4. The sample receptacle of claim 3 wherein the means for cooling the sample chamber comprises means for fluid flow in contact with the tubular member.

5. The sample receptacle of claim 3 wherein the means for cooling the sample chamber comprises a jacket enclosing and spaced apart from at least a major portion of the length of the tubular member so as to form an annular space between the tubular member and the jacket.

6. The sample receptacle of claim 5 in which the means for cooling the sample chamber further comprises a cooling fluid inlet and a cooling fluid outlet.

7. The sample receptacle of claim 1 in which the sample inlet and the sample outlet are circular orifices and the sample outlet has a diameter at least as great as the diameter of the sample inlet.

8. The sample receptacle of claim 3 in which the sample outlet is approximately equal in diameter to the diameter of the cylindrical bore.

9. The sample receptacle of claim 5 in which the annular space contains means to direct the flow of a fluid flowing therein.

10. The sample receptacle of claim 9 in which the directing means comprises a spiraling baffle extending along the length of the tubular member.

11. The sample receptacle of claim 1 which further comprises means for attaching the outlet end of the tubular member to an inlet port of a gas chromatograph.

12. A sample injection system for an analytical instrument comprising a first sample chamber and a second sample chamber, means for cooling the first sample chamber, and means for introducing a carrier gas into the first sample chamber, the first sample chamber having a first sample inlet for receiving a solid sample and an opposing sample outlet for removal of a solid sample, and the second sample chamber having a second sample inlet for receiving a solid sample and a gas outlet, wherein the sample outlet extends openly into the second sample inlet so as to provide means for gas flow and solid sample transfer from the first sample chamber to the second sample chamber.

13. The injection system of claim 12 in which the sample outlet opens into an intermediate chamber having an internal diameter equal to that of the sample outlet and thence into a second sample inlet having a diameter equal to that of the intermediate chamber.

14. The injection system of claim 12 in which the means to cool the first chamber comprises a jacket substantially enclosing and spaced apart from the first sample chamber so as to form an annular space between the first sample chamber and the jacket, a cooling gas inlet to the annular space and a cooling gas outlet from the annular space.

15. The injector system of claim 14 in which the first and second sample chambers comprise a tube of essentially constant interior diameter extending from the first sample inlet to the gas outlet of the second sample chamber, the first sample chamber being defined by the length of the tube enclosed in the jacket.

16. The injection system of claim 15 in which the annular space contains baffle means.

17. The injection system of claim 16 which further comprises at least one conduit from the gas outlet of the second sample chamber.

18. The injection system of claim 15 in which the intermediate chamber is defined by a lesser exterior tube radius than the exterior tube radius of the second sample chamber.

19. The injection system of claim 15 which further comprises exterior means to secure the injector port within an analytical instrument.

20. A method for thermal analysis of a sample selected from a solid and a liquid wherein the sample is exposed to an elevated temperature effective for volatilizing at least a portion of the sample and the resulting products are passed in a carrier gas stream to at least one detecting means capable of producing a signal responsive to a change in the composition of the carrier gas stream, the method comprising:
   introducing a measured sample into a first chamber which is in carrier gas flow communication with said detecting means and which is maintained at a temperature lower than said elevated temperature;
   allowing the carrier gas to flow across the sample to the detecting means for a time effective for establishing a substantially stable response signal representative of the carrier gas;
   subsequently transferring the sample from the first chamber to a second adjoining chamber which has been preheated to said elevated temperature and heating the sample to said elevated temperature thereby producing a gaseous product; and passing said gaseous product in the carrier gas stream to the detecting means and producing a signal indicative of the presence of the gaseous product.

21. The method of claim 20 in which the detecting means comprises a flame ionization detector.

22. The method of claim 21 in which the carrier gas is helium.

23. The method of claim 20 in which the sample is transferred from the first chamber to the second chamber via an intermediate insulating chamber.

24. The method of claim 20 which further comprises the steps of heating the remaining portion of the sample to a second elevated temperature effective for pyrolyzing the sample, thereby producing pyrolysis products, and passing said pyrolysis products in the carrier gas stream to the detecting means and producing a second signal indicative of the presence of the pyrolysis products.

25. The method of claim 24 in which the detecting means comprises a flame ionization detector and the carrier gas is helium.

26. The method of claim 20 in which the sample is retained in the first chamber for at least one minute.

27. The method of claim 24 in which the sample is transferred from the first zone to the second zone by means of a sample insertion device having a radiant heater and the pyrolysis of the sample is accomplished with the radiant heater.

28. A method for the thermal analysis of a geological sample wherein the sample is exposed to an elevated temperature effective for volatilizing at least a portion of the sample, the method comprising:

introducing a measured geological sample into a first chamber which is in carrier gas flow communication with a detecting means capable of producing a signal responsive to a change in the composition of the carrier gas stream, said first chamber being maintained at a temperature which is lower than said elevated temperature;

allowing the carrier gas to flow in contact with the sample and thence to the detecting means for a time effective for establishing a substantially stable response signal respresentative of the carrier gas;

subsequently transferring the sample from the first chamber to an adjoining second chamber which has been preheated to said elevated temperature and heating the sample to said elevated temperature thereby producing a thermal extraction product; and passing said thermal extraction product in the carrier gas stream to the detecting means and producing a signal indicative of the presence of the thermal extraction product.

29. The method of claim 28 in which the geological sample is selected from rock and kerogen.

30. The method of claim 29 in which the detecting means is a flame ionization detector.

31. The method of claim 29 in which the elevated temperature is within the range of about 250° C. to about 310° C.

32. The method of claim 31 in which the sample is retained in the first chamber for a time of about 1 to 2 minutes.

33. The method of claim 31 in which the temperature of the first chamber is from about 30° C. to about 40° C.

34. The method of claim 28 in which the sample is transferred from the first chamber to the second chamber via an intermediate insulating chamber.

35. The method of claim 28 further comprising the steps of heating the remaining portion of the sample to a second elevated temperature effective for pyrolyzing the sample, thereby producing pyrolysis products, passing said pyrolysis products in the carrier gas stream to the detecting means and producing a second signal indicative of the presence of the pyrolysis products.

36. The method of claim 35 in which the second elevated temperature is within the range of about 350° C. to about 1000° C.

37. The method of claim 36 in which the sample temperature is increased from the first elevated temperature to the second elevated temperature at a constant rate.

38. The method of claim 37 in which the sample temperature is increased from the first elevated temperature to the second elevated temperature at a rate of from about 30° C./min to about 300° C./minute.

39. The method of claim 36 in which the sample is pyrolyzed by means of a radiant heater on a sample insertion device.

40. The method of claim 36 in which the sample is retained in the first chamber for a time of from about 1 minute to about 2 minutes.

41. The method of claim 36 in which the first and second response signals are recorded graphically as a function of time.

42. The method of claim 36 in which the first and second response signals are recorded and are used to determine the petroleum-generating potential of the geological sample.

* * * * *